United States Patent [19]
Kauzlarich

[11] Patent Number: 5,571,952
[45] Date of Patent: Nov. 5, 1996

[54] ELECTRONIC VISCOMETER

[75] Inventor: James J. Kauzlarich, Charlottesville, Va.

[73] Assignee: University of Virginia Patent Foundation, Charlottesville, Va.

[21] Appl. No.: 418,112

[22] Filed: Apr. 6, 1995

[51] Int. Cl.$^6$ ................................................ G01N 11/10
[52] U.S. Cl. ........................................ 73/54.24; 73/54.26
[58] Field of Search .............................. 73/54.41, 54.25, 73/54.26, 54.27, 54.28, 54.23, 54.24

[56] References Cited

U.S. PATENT DOCUMENTS

| | | |
|---|---|---|
| 2,839,915 | 6/1958 | Roth . |
| 3,062,040 | 10/1959 | McKennell et al. ................... 73/54.24 |
| 3,587,295 | 6/1971 | Simons ................................... 73/54.41 |
| 3,710,614 | 1/1973 | Oppliger . |
| 3,712,117 | 1/1973 | Fitzgerald et al. . |
| 4,425,810 | 1/1984 | Simon et al. . |
| 4,524,610 | 6/1985 | Fitzgerald et al. . |
| 4,580,574 | 4/1986 | Gavish . |
| 4,721,874 | 1/1988 | Emmert . |
| 4,779,452 | 10/1988 | Cohen-Tenoudji et al. . |
| 4,799,378 | 1/1989 | Portman . |
| 4,811,593 | 3/1989 | Miura . |
| 4,862,384 | 8/1989 | Bujard . |
| 4,878,378 | 11/1989 | Harada . |
| 4,905,499 | 3/1990 | Miura et al. . |
| 4,909,068 | 3/1990 | Miura et al. . |
| 4,920,787 | 5/1990 | Dual et al. . |
| 4,922,745 | 5/1990 | Rudkin et al. . |
| 4,926,682 | 5/1990 | Holm-Kennedy et al. . |
| 4,994,703 | 2/1991 | Oguri et al. . |
| 5,025,656 | 6/1991 | Wright . |
| 5,067,344 | 11/1991 | Fitzgerald et al. . |
| 5,157,962 | 10/1992 | Fitzgerald et al. . |
| 5,201,215 | 4/1993 | Granstaff et al. . |
| 5,228,331 | 7/1993 | Odagiri et al. . |
| 5,301,540 | 4/1994 | Pilacinski et al. . |

OTHER PUBLICATIONS

Kirk-Othmer; Encyclopedia of Chemical Technology; Third Edition, vol. 10, p. 24; Ferroelectrics to Fluorine Compounds, Organic; A Wiley-Interscience Publication, John Wiley & Sons.
A New Method for Continuous Viscosity Measurement. General Theory of the Ultra-Viscoson; Journal of Applied Physics; vol. 24, No. 7, Jul. 1953, pp. 940–950; W. Roth and S. Rich.
Encyclopedia of Electronics; p. 646; 2nd Edition; Stan Gibilisco, Neil Sclater, Co-Editors-in-Chief; TAB Professional and Reference Books.
Singman, A.; *Popular Electronics*, Mar. 1994, 69.
Lamb, H., Proc. Roy. Soc. A, V.98, 1921, pp. 205–216.
Tipei, Theory of Lubrication, Oxford, 1962.
Product Brochure: Physica-Rheoswing.
Measurement of the Viscosity and Shear Elasticity of Liquids by Means of a Torsionally Vibrating Crystal; Transactions of the A.S.M.E., May, 1947.
Rheology-Theory and Applications, vol. 3, 1960 Academic Press.
All About Piezoelectric Elements, A. Singmin; Popular Electronics, Mar. 1994.
Product Brochure–Bohlin Visco 88.
Product Brochure–The Bohlin Controlled Stress Rheometer.
Product Brochure–The Bohlin VOR Rheometer.
Product Brochure–Bohlin DSR-F Rheometer.
Product Brochure–Bohlin CVO Rheometer.

*Primary Examiner*—Hezron E. Williams
*Assistant Examiner*—Jay L. Politzer
*Attorney, Agent, or Firm*—Oblon, Spivak, McClelland, Maier & Neustadt, P.C.

[57] ABSTRACT

An electronic viscometer having a vibrating drive and a hollow probe. The hollow probe oscillates along its longitudinal axis, and is damped by a sample into which it is inserted.

6 Claims, 2 Drawing Sheets

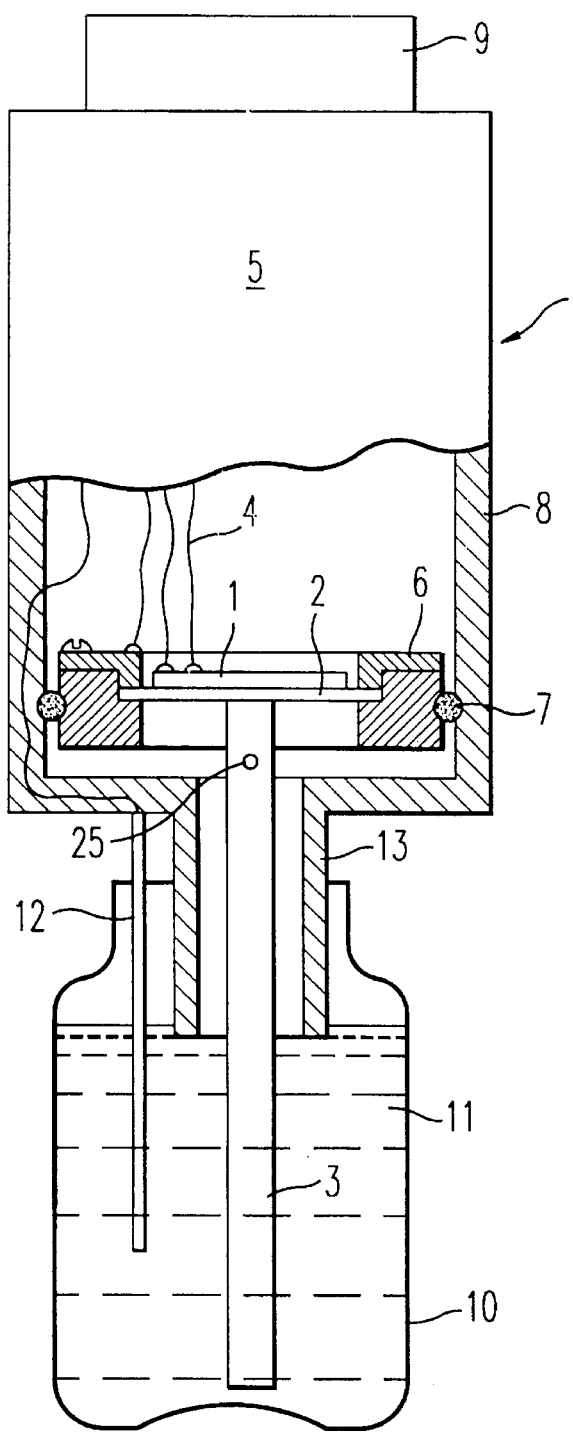
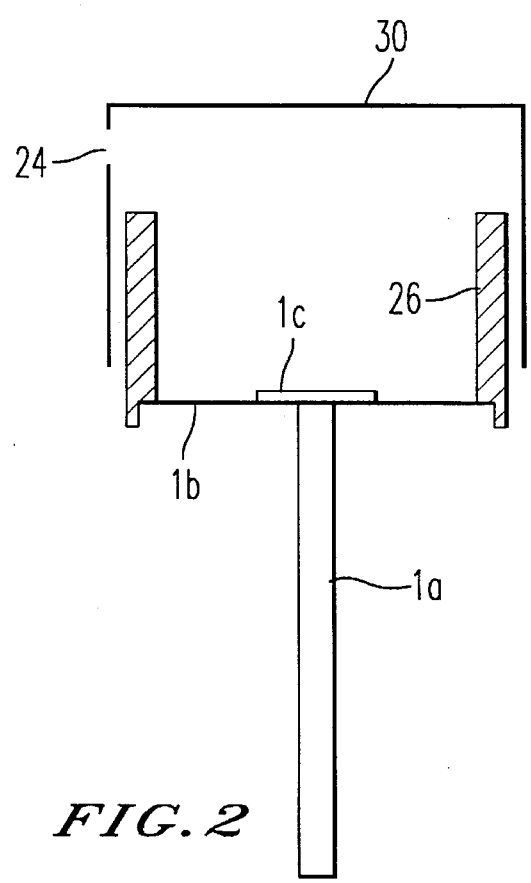
FIG. 1
FIG. 2

ELECTRONIC VISCOMETER

FIELD OF THE INVENTION

The present invention relates to an electronic viscometer comprising vibrating drive means and a hollow, preferably tubular, viscosity probe. The vibrating drive means causes the probe to vibrate, preferably axially (i.e., along a longitudinal axis) and without motion in other directions, so as to set up shear waves in a sample whose viscosity is being measured. Damping of the probe's motion is related to viscosity.

BACKGROUND OF THE INVENTION

Sample viscosity is often a critical parameter in the paint industry, food industry, pharmaceutical and cosmetic industries, plastics, polymer and petrochemical industries, medical/biochemical industries, etc., and devices for measuring the viscosity of fluids have been in existence for many years. One common viscometer type is the oscillatory viscometer, which measures sample viscosity by determining the amount of damping experienced by a moving probe immersed in a sample fluid.

J. G. Woodward, a pioneer in the field, developed one of the first oscillatory viscometers in 1953 (*The Journal of the Acoustical Society of America*, 25, 147–151, 1953, incorporated herein by reference). Woodward measured the amount of damping experienced by an oscillating plate immersed in a fluid, and developed a mathematical relationship between the damping and fluid viscosity. His calculations are still used today for oscillating probe viscometers.

Also in 1953, Roth and Rich described and later patented an apparatus and method for measuring the viscosity of fluid-like materials using an elongated strip of magnetorestrictive material vibrated by transducer coils. See *J. Appl. Phys.*, Vol. 24, No. 7, 1953 and U.S. Pat. No. 2,839,915, both incorporated herein by reference. In both references a solid rectangular strip was used as a sample probe which oscillated in the longitudinal compressional mode.

In 1989, Portman (U.S. Pat. No. 4,799,378, incorporated herein by reference) disclosed a piezoelectric viscometer using, as a viscosity probe, a quartz reed with a ball formed on the end thereof. The vibratory motion of the piezoelectric element caused the probe to oscillate. The Portman viscometer, like the Roth viscometer, is a device wherein the viscosity probe's range of motion is approximately 1 mm or more, however, the measurement of viscosity in such a system depends upon viscous flow theory.

Several viscometers have been developed using probes which undergo a twist vibration (i.e., a torsional mode of vibration) about a central axis. Miura (U.S. Pat. No. 4,811,593, incorporated herein by reference), disclosed such an instrument in 1989 using a transmission shaft that, via twist vibration, detects the viscous resistance offered by a liquid sample. The Paar Physica U.S.A. Physica-Rheoswing® commercial rheometer uses such torsional oscillations in determining dynamic and kinematic viscosity.

Harada, also in 1989, described a rotating viscometer wherein a rotary member spins within a fixed housing, causing the sample whose viscosity is being measured to flow. See U.S. Pat. No. 4,811,593, incorporated herein by reference. The Bohlin Visco 88® viscometer utilizes this general configuration by providing a rotating inner cylinder and a stationary outer cylinder.

Even with this great diversity in viscometer design, however, no viscometer to date has successfully combined the attributes of simple design, portability, field toughness, low cost and accuracy. Portability and field toughness are particularly advantageous for applications which include the need to measure the viscosity of a sample outside of a laboratory setting, such as the viscosity of a drilling mud on an off-shore oil rig. Sending samples back and forth to a laboratory for viscosity determination can be tedious and time-consuming, and can significantly slow down work already in progress. That a viscometer needs to be accurate is self-evident. Low cost, of course, if it can be combined with portability and accuracy, is also clearly desirable. Unfortunately, current commercially available viscometers are expensive, ranging in cost from about $7,000 to $25,000.

OBJECTS OF THE INVENTION

Accordingly, one object of the present invention is to provide an electronic viscometer which overcomes the drawbacks of the prior art by, e.g., combining portability, low cost and accuracy.

Another object of the present invention is to provide a viscometer having a vibrating drive and a tubular probe.

Another object of the present invention is to provide an electronic viscometer that induces shear waves in a sample being measured with an oscillating hollow probe, the oscillating hollow, preferably tubular probe being set into oscillation (vibration) by a piezoelectric drive, preferably a piezoelectric crystal.

Another object of the present invention is to provide a viscometer which determines the viscosity of a liquid by providing a measurement of the product of absolute viscosity, density and frequency.

Another object of the present invention is to provide an electronic viscometer whose probe oscillates substantially in the axial mode, most preferably in only the axial mode (motion along the long axis of the probe).

Another object of the present invention is to provide an electronic viscometer having computational means for converting the viscosity density frequency product into either density or absolute viscosity.

Another object is to provide a tubular viscosity probe having a sharp edge on that end which is to be immersed in a sample to have substantially viscous shear only, and having a hole in the wall of the probe, located away from the end with the sharp edge and above the surface of the sample being measured to allow the sample in the tube to reach the same level as the sample outside the tube.

BRIEF DESCRIPTION OF THE DRAWING

These and other objects will become apparent as the present invention becomes better understood by reference to the following detailed description and Figures.

FIG. 1 is an electronic viscometer according to the present invention;

FIG. 2 shows a structure of another embodiment of an electronic viscometer according to the present invention.

DETAILED DESCRIPTION OF THE PREFERRED EMBODIMENTS

Figure 3:
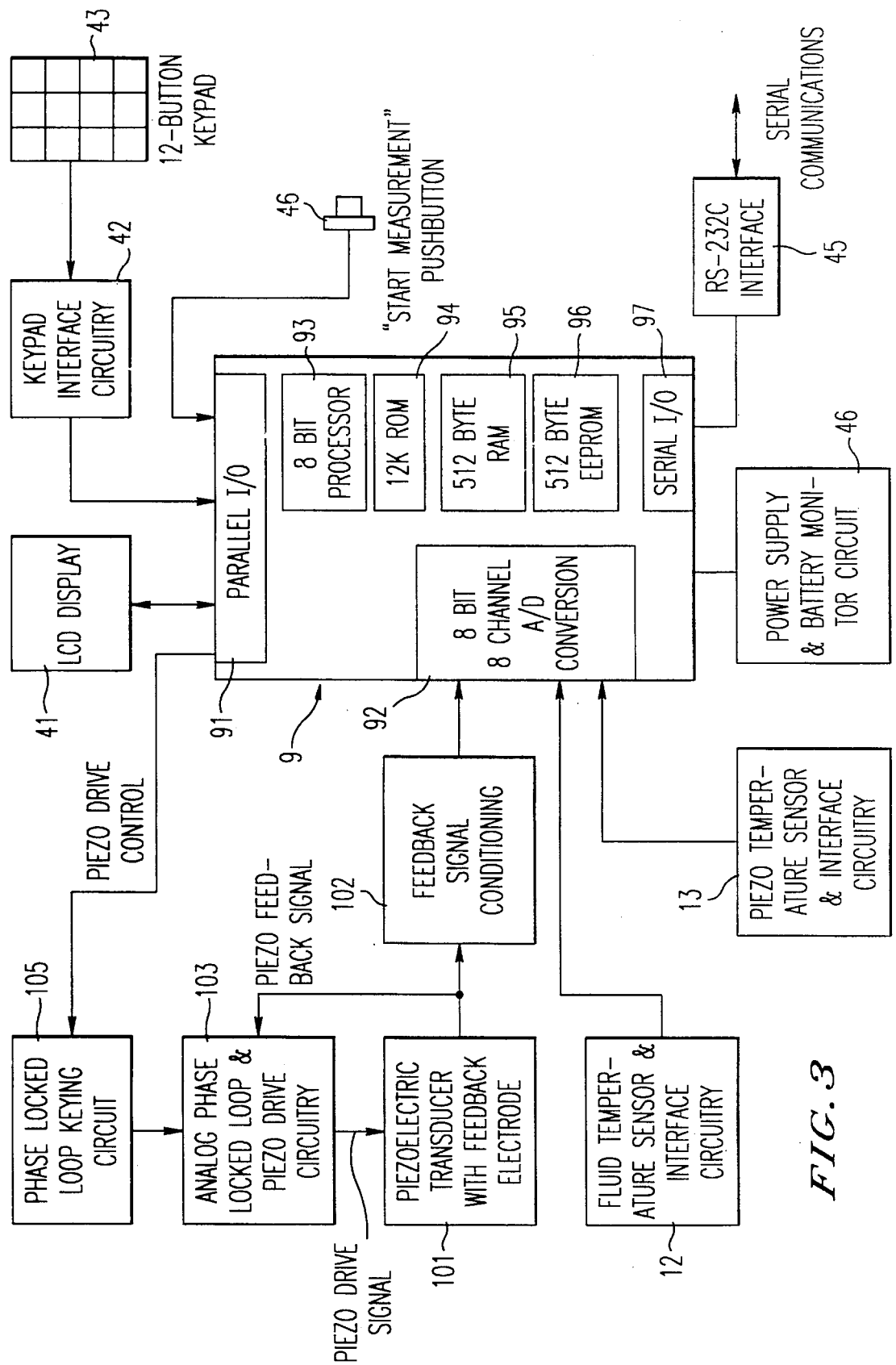
FIG. 3 is a schematic of an electronic circuit configuration illustrating the electronics of the viscometer of FIG. 1.

In FIG. 1 a preferred electronic viscometer according to the present invention is shown comprising piezoelectric crystal 1 on plate 2, hollow tube 3 having a vent near the top of the tube. Tube 3 is attached to the center of the plate and is perpendicular thereto. Wires 4 lead to and away from the piezoelectric crystal surface and to and away from electronic components 5 which supply oscillating voltage to drive the piezoelectric crystal. Metal holder 6 holds plate 2 and is supported by O-ring 7. External housing 8 contains computing means 9. The tube is immersed in a sample being measured 11 contained in bottle 10 to a specific depth, controlled by immersion control tube 13. Thermocouple 12 measures the sample temperature and is provided with a lead to the electronic components.

FIG. 2 shows another preferred electronic viscometer according to the present invention. Here the piezoelectromechanical drive and probe assembly including tube 1a, plate 1b and piezocrystal 1c is attached to a brass tube (2) having an O.D. of 1.5 in. The probe assembly plate 1b has an O.D. of 1.38 in. and is soldered to the edge provided in (2). A covering (3) is provided with port (4) for connections to the separate electronic components (not shown).

The present invention electronic viscometer comprises a vibrating drive which causes a viscosity probe to oscillate. The invention vibrating drive preferably is capable of oscillating the viscosity probe at a natural frequency of from 500 to 3000 Hz, preferably 1000–2000 Hz at an amplitude ranging from $1 \times 10^{-4}$–$1 \times 10^{-1}$ mm, preferably $1$–$10 \times 10^{-3}$, most preferably approximately $9 \pm 20\%$ $5 \times 10^{-3}$ mm, in air. In this way the damping of the oscillations of the viscosity probe by the sample being measured is dependent upon wave mechanics (Eirich, F. R., *Rheology Theory and Applications*, V.3, Academic Press, 1960, pp. 65–70) rather than newtonian fluid mechanics or Lamb's plate mechanics (Lamb, *Proc. Roy. Soc. A*, V.98, p. 205, 1921), both references incorporated herein by reference. Any vibrating drive capable of driving a viscosity probe in this manner, either directly or in attenuated or amplified fashion, is acceptable and is included within this invention. However, a particularly preferred drive is a piezoelectromechanical drive having a feedback portion.

As will be further described below, piezoelectromechanical drives provide several advantages over other types of vibratory drives and are based on piezoelectric crystals. Once subjected to mechanical stress these materials produce electric currents, and when subjected to an electric voltage piezoelectric crystals vibrate. Piezoelectric substances useful in the present invention drive means include quartz, Rochelle salts and various piezoelectric ceramics. Preferred is a 25 mm diameter piezoelectric crystal made of ceramic and sintered to a thin brass plate having a 35 mm diameter, a feedback electrode and resonating at 2.8 khz sold by MPS (Great Britain). Other piezoelectric materials useful in the present invention vibrating drive include lithium niobate, and the piezoelectric materials in "Piezoelectric Ceramics" by E. Kolm in *Mechanical Engineering*, February, 1984, p. 43, incorporated herein by reference. Further examples of piezoelectric elements useful in the present invention as vibrating drive means are described in Singman, *Popular Electronics*, p. 69, March, 1994, incorporated herein by reference and in U.S. Pat. Nos. 4,799,378, 4,994,703, 4,920, 787 and 4,811,593, all incorporated herein by reference.

The vibrating drive of the present invention electronic viscometer preferably is capable of imparting pure or substantially pure axial motion to the viscosity probe at the natural frequency for this motion (e.g., 1.5 kHz) (i.e., motion along a longitudinal axis of the probe) with a frequency and amplitude as described above, and provides a feedback voltage that can be used to calculate the product of viscosity and density.

The viscosity probe of the present invention electronic viscometer is that part of the viscometer which is inserted into the sample being measured, preferably fluids or fluid-like samples including paint, oil, water, etc. Preferably, the viscosity probe has a longitudinal axis and is hollow, and is preferably hollow, and is preferably a hollow tube having a circular cross section, a longitudinal axis, and an aspect ratio (length divided by outside diameter) of from 1.5 to 15, preferably 10 to 13, more preferably 10.2 to 11. The thickness of the tubular wall is preferably uniform and is from 0.005 to 0.035, preferably 0.010 to 0.015 (inches) thick. Regardless of the probe shape and cross section it is preferred to have one long axis only and be capable of being described by an overall aspect ratio (long axis (length) divided by shortest axis (width). The wall at the end portion of the probe which is to be inserted into a sample to effect viscosity measurement is preferably tapered or sharpened (pointed) in order to reduce compressional effects and maximize shear forces produced by pure or substantially pure axial probe motion (i.e., a motion wherein the tube vibrates or oscillates along only its long axis in a piston-like motion, the end of the tube remaining in the sample throughout the measurement).

The hollow viscosity probe can include within its wall at least one vent hole in any shape including the shape of a circle, square, etc., which allows for the escape of trapped air when one end of the probe is inserted into a fluid or fluid-like sample. In this manner the sample is able to rise up within the probe to the same or approximately the same sample level as is present along the outside wall of the probe. Preferred probe inner diameters range from 0.189 inches to 0.25 inches, preferably 0.19 to 0.22 inches, preferred probe lengths range from 2.3 to 3.0 inches, preferably 2.5 to 2.75 inches.

The invention hollow viscosity probe may be made from any material, including plastic, metal, ceramic, etc. Metal tubes are preferred. Any material that can maintain a hollow and/or tubular shape and be driven in a pure or substantially pure axial motion within the frequency and amplitude ranges described above may be utilized. Other hollow probe shapes include square, rectangle, triangle, oval, etc. cross-sections. All the invention probes have a longitudinal axis and present an inside and an outside surface for contact with the sample to be measured.

The viscosity probe may be connected to the vibrating drive means in any convenient fashion as long as the vibrations from the drive means are transferred to the probe. The viscosity probe may be directly connected to the vibrating drive means, or vibration transferring, attenuating or amplifying means may be inserted between the drive and the probe.

In a preferred embodiment, the vibrating drive means comprises a piezoelectric crystal, the viscosity probe is a thin-walled brass tube sharpened at that end which is to be inserted into the sample, and a circular brass plate is inserted between the probe and crystal as connecting means. The piezoelectric crystal is attached to one side of the brass plate and the tube is attached to the other side and oriented perpendicular thereto. The piezoelectric crystal is attached to the brass plate by sintering, and the thin tube is attached to the other side of the brass plate by, e.g., solder. Pure axial motion is then provided by driving the crystal/plate/tube system at the natural frequency mode that gives this motion.

Of course, the plate need not be brass, and other materials including nickel, stainless steel, Ni-Span alloy 902, etc. may also be used. Ni-Span alloy 902 would probably introduce no temperature dependance. To increase accuracy, it is preferred that the invention viscometer have heating/cooling means capable of providing the drive and probe at substantially the same temperature (±10°, preferably ±3° or less), preferably at the temperature of the sample being measured. Examples of such heating/cooling means include heat pumps, refrigeration units, resistance heaters, fans, ice blocks, etc.

Other means for attaching the viscosity probe, including a tubular probe, to a plate include welding, brazing, gluing, etc.

The plate, if used, can be of any shape but is large enough to support (preferably completely) the piezoelectric crystal and is at least as big as the outer diameter of the hollow viscosity probe. The plate is preferably circular, having a preferred diameter of from 1.25–1.75 inches, most preferably 1.3–1.4 inches and a preferred thickness of from 0.015–0.025 inches, preferably 0.01–0.02 inches. The plate can be supported in various ways and in various housings, etc. It has been discovered that the response of the invention viscometer can be improved by varying the support, i.e., by changing the distance between the probe and support points along or around the plate. In addition, a plate that varies in thickness along its radius can provide improved results. For example, a circular plate which is thinner at its outer edge (e.g. 1–2 mm thick) and twice as thick in the center as at the edge having a tubular probe bonded thereto works very well with a circular support from above or below, the support having a circular edge of 1.85 mm diameter supporting the plate. The plate dimensions and where and how it is supported can thus be varied to maximize the amplitude of the probe motion.

The invention electric viscometer includes electronic components capable of driving the viscometer's vibrating drive means at the resonant frequency associated with the pure or substantially pure axial vibration of the viscosity probe. The circuit drives the vibrating drive means, preferably a piezoelectric crystal, at a constant or approximately constant voltage (required for the measurement of the product of the absolute viscosity and density). The driving circuit is preferably a square wave providing a constant RMS value driving voltage to the piezoelectric crystal which, in turn, provides a constant driving force to the viscosity probe. A sinusoidal feedback voltage is generated by a feedback portion of the vibrating drive means, and this voltage is a measure of the amplitude of the viscosity probe. The ratio of amplitudes of the viscometer probe as measured in air (essentially undamped) as compared to that measured when inserted into a fluid sample of interest provides a measure of damping which can be used to calculate the product of absolute viscosity and density. That is, the damping of the viscometer tube when placed in a sample being measured is proportional to the feedback voltage of the vibrating drive, preferably a piezoelectric crystal. The circuit is self-oscillating. Examples of circuits useful in the present invention electronic viscometer are described in FIG. 4 of Singman, *Popular Electronics*, p. 69, March, 1994, incorporated herein by reference and in FIG. 12 of U.S. Pat. No. 4,905,499, the whole patent incorporated herein by reference. In addition, further useful circuits are described in Horowitz, P. and Hill, W. *The Art of Electronics*, 2nd Ed.; Cambridge Univ. Press, 1989, pp. 641–655, the entire reference incorporated herein by reference.

In addition to measuring the amplitude of vibration and subsequent damping in a sample to be measured, the absolute viscosity and density product of a sample may be obtained by measuring the phase shift of the drive means input and output signal. See, for example, U.S. Pat. No. 4,922,745, incorporated herein by reference, particularly columns 6 and 7 thereof.

In addition to the electronic circuitry which operates the vibrating drive means, a temperature circuit comprising a simple thermocouple, thermistor, etc. may optionally be provided to determine the temperature of the sample being measured before, during and/or after measurement. For accuracy, the temperature of the sample is necessary since most fluid's viscosity is temperature dependent.

In addition to the electronic circuits described above the present invention electronic viscometer preferably comprises computation means (i.e., a computer, microprocessor, etc.) which will calculate the absolute viscosity and density product according to the following formula:

$$\eta\rho = K\left(\frac{f_{air}}{f}\right)\left[\frac{F_{air}Y_{air}}{fY} - 1\right]^2 \qquad \text{Eq. 1:}$$

where n=the absolute viscosity p=the density or specific gravity

K=a constant for the instrument $f_{air}$=the resonate frequency with the probe in air f=the resonate frequency with the probe in the sample $Y_{air}$=the resonate amplitude with the probe in air Y=the resonate amplitude with the probe in the sample Finally, the electronic viscometer according to the present invention is preferably, but optionally, contained within a housing and isolated therefrom via springs, an O-ring, rubber gasket, etc. The housing may include an immersion control tube through which the viscosity probe exits the housing, the length of the immersion control tube being chosen such that, when the electronic viscometer is immersed in a sample up to the end of the immersion control tube, the viscosity probe, extending beyond the immersion control tube, is inserted into the sample into the desired depth. See FIG. 1. Without such a control tube a simple mark on the probe may be used. The electronic components can be contained in the viscometer housing or in a separate area connected to the viscometer probe head by wires, etc.

EXAMPLE

A piezoelectric crystal obtained from MPS Great Britain and described as a "Piezo Transducer 35 mm/2.8 Khz with feedback electrode" was used as the vibrating drive means. The crystal is 25 mm in diameter is sintered to a brass plate (circular) of 35 mm diameter, resonates at 2.8 Khz, contains a feedback electrode, has a maximum voltage of 30 volts and an impedance at resonance of 450Ω. A hollow brass tube was provided as the viscosity probe having a ¼ inch outer diameter, a 0.15 inch thick wall, a length of 65 (mm) and a sharpened end intended for insertion into a fluid sample. The tube also had a vent hole in the wall thereof near the non-sharpened edge.

A circular brass plate 57 mm OD (19 mm thick) having a 34 mm diameter hole in the center thereof was provided as support and the crystal/brass plate (diameter=35 mm, thickness=0.03 mm) was glued thereto by means of epoxy and the tubular probe was glued to the MPS brass plate bottom with epoxy and oriented perpendicular thereto. A rubber O-ring having a diameter of 2.0 inches was placed on the underside of the brass support for vibration isolation, and this structure was then supported by an aluminum plate and ring stand, the probe protruding through the hole in the supporting plate, the lead wires of the crystal protruding from the top of the probe head. The device, supported in a ring stand, allowed for the probe to be inserted into a sample. A thermocouple was also provided.

An electronic circuit was provided which delivered a constant input voltage at the probe's resonant frequency (~1.7 kHz). The electronic equipment involved commercial devices as follows. A Krohn-Hite frequency generator was used to supply the crystal at the resonant frequency and control the amplitude of vibration. A Hewlett-Packard universal counter was used to measure the driving frequency. H-P (Hewlett-Packard) digital multimeters, oscilloscope, and strip chart recorder were used to measure the feed back voltage from the crystal and temperature of the thermocouple; the thermocouple was connected to an Omega thermocouple meter and output to the strip chart recorder.

In making a measurement, the resonant frequency in air of the crystal-probe device was determined and the driving voltage made constant for subsequent testing. The probe was then inserted in the test fluid to a specific length on the probe and the feedback voltage and frequency was measured. Since the test fluid viscosity and density are known, the results can be used to determine a device calibration constant K. The device was further tested using a variety of test fluids for which the viscosity and density were known to verify that the device operated in accordance with theory. Once this work was completed the device can be used to measure the viscosity and density product. By knowing the fluid density from a density measurement, the viscosity can be extracted from the invention device reading of the viscosity and density product. In the case of mineral oils and other fluids it is possible to derive equations relating the viscosity and density to the ISO number for the oil or some other physical characteristic and by a mathematical calculation the viscosity as well as the density can be determined from the invention instrument output at the measured temperature of the test fluid.

Microprocessor control of the piezoelectric viscometer of either the embodiment of FIG. 1 or FIG. 2 is shown in block diagram form in FIG. 3 which is built around the computer structure 9. The computer 9 is typically an 8-bit microcontroller having an 8 bit 8 channel A/D (analog/digital) converter 92 as well as an 8 bit processor 93 and in the embodiment illustrated a 12K ROM with a 512 byte RAM 95 and a 512 byte EEPROM 96. A serial I/O 97 is connected to a RS-232C interface 45 to provide serial communication and a parallel I/O interface 91 is connected to a liquid crystal display 41 and to a key pad interface circuitry 42 for ultimate connection to a key pad 43 as well as a start push button 46. Also connected to the parallel input/output 91 is a piezoelectric drive control fed to a phase locked loop keying circuit 105 which in turn is connected to an analog phase of the locked loop and piezoelectric drive circuitry 103. The piezoelectric drive circuitry provides a drive signal to the piezoelectric transducer which has a feedback connection to the drive circuitry 103. The feedback signal is also conditioned at 102 and fed to the A/D converter 92. Other measurements include the fluid temperature sensor and interface circuitry 12 and the piezoelectric temperature sensor and interface circuitry 13 which are also fed to the A/D converter. The entire system is controlled by a power supply and battery monitor circuit 46. A known test fluid is used to determine the instrument constant of the device K. With K known and the equation for frequency ratio versus amplitude ratio determined for the device the device will properly calculate the viscosity and density of a fluid sample or give a reading for the product of viscosity and density for which the viscosity can be extracted by measuring the density separately.

What is claimed as new and desired to be secured by Letters Patent of the United States is:

1. An electronic viscometer, comprising:

a piezoelectric crystal attached to a first side of a metal plate, said plate made of a material selected from a group consisting of nickel, brass and steel;

a hollow circular tube having a first end attached to a second side of said plate, said tube having a longitudinal axis perpendicular to said second side, said tube made of a material selected from a group consisting of brass, steel, aluminum, ceramics and glass;

said piezoelectric crystal being driven by piezoelectric drive means and having a feedback electrode for providing a feedback signal, wherein said piezoelectric crystal receives an input signal and provides an exclusive longitudinal vibratory motion to said tube and wherein at least a second end of said tube has a sufficiently thin wall to maximize shear forces produced by said exclusive longitudinal vibratory motion when said second end is inserted in a liquid whose viscosity is to be measured;

and wherein the aspect ratio of said tube is chosen so as to provide said exclusive longitudinal vibration motion when said piezoelectric crystal is driven by an oscillating constant root mean square value driving voltage.

2. The viscometer as claimed in claim 1 wherein said aspect ratio is between 1.5 and 15.

3. The viscometer as claimed in claim 1 wherein said tube includes an air vent which allows for the escape of trapped air when said one end of said tube is inserted into said fluid.

4. The viscometer according to claim 1 wherein said tube oscillates at a frequency of from 500 to 3,000 Hz.

5. The viscometer according to claim 4 wherein said frequency is between 1 and 2 KHz.

6. The viscometer according to claim 1 further including temperature measurement means for providing said piezoelectric crystal at substantially the same temperature as said fluid whose viscosity is being measured.

\* \* \* \* \*